United States Patent
Choi et al.

(10) Patent No.: US 7,105,630 B2
(45) Date of Patent: Sep. 12, 2006

(54) COMPOUND HAVING THERMALLY DISSOCIATABLE THIOACETAL SKELETON, PRECURSOR THEREOF, CURED PRODUCT THEREOF, AND COMPOSITION FOR THEIR PRODUCTION

(75) Inventors: Wonmun Choi, Kanagawa (JP); Hiroyuki Okuhira, Kanagawa (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 0 days.

(21) Appl. No.: 10/416,030

(22) PCT Filed: Sep. 10, 2002

(86) PCT No.: PCT/JP02/09225

§ 371 (c)(1),
(2), (4) Date: May 7, 2003

(87) PCT Pub. No.: WO03/022802

PCT Pub. Date: Mar. 20, 2003

(65) Prior Publication Data

US 2004/0014935 A1    Jan. 22, 2004

(30) Foreign Application Priority Data

Sep. 10, 2001  (JP)  ............................ 2001-273220
Dec. 11, 2001  (JP)  ............................ 2001-376810
Dec. 14, 2001  (JP)  ............................ 2001-381190

(51) Int. Cl.
    *C08G 75/04*  (2006.01)
(52) U.S. Cl. .................. 528/374; 528/380; 568/57
(58) Field of Classification Search ............ 528/380, 528/374; 568/57
    See application file for complete search history.

(56) References Cited

U.S. PATENT DOCUMENTS 2,527,377 A * 10/1950 Patrick .................. 568/56
3,413,265 A * 11/1968 Bertozzi .................. 528/12
4,837,271 A    6/1989 Brindopke
5,654,368 A    8/1997 Nakano et al.
5,733,965 A * 3/1998 Scholl et al. ............ 524/513

FOREIGN PATENT DOCUMENTS

| JP | 04-175375 | A1 | 6/1992 |
| JP | 07-082351 | * | 3/1995 |
| JP | 07-082351 | A1 | 3/1995 |
| JP | 07-082514 | * | 3/1995 |
| JP | 07-082514 | A1 | 3/1995 |
| JP | 08-085736 | A1 | 4/1996 |
| JP | 09-59393  | A1 | 3/1997 |

OTHER PUBLICATIONS

International Search Report for PCT/JP02/09225 mailed on Jan. 14, 2003.

* cited by examiner

Primary Examiner—Porfirio Nazario-Gonzalez
Assistant Examiner—Chukwuma Nwaonicha
(74) Attorney, Agent, or Firm—Rader, Fishman & Grauer PLLC

(57) ABSTRACT

A compound having thioacetal skeleton, a precursor thereof, a cured product thereof, and a composition for their production are provided for the thermally dissociatable material based on the inventors' finding that a thioacetal group is thermally dissociatable. The use of the thermally dissociatable material of the invention enables softening or liquefaction at any desired timing through thermal dissociation at a temperature below the thermal decomposition temperature of the cured product. It is thus possible to disassemble the structure to which the thermally dissociatable material had been attached in a short time. The thermally dissociatable material is useful as a highly disposable plastic material and is adapted for use as a sealant, coating composition or adhesive. Such material may be used, for example, as a curing agent for urethane curable composition or epoxy curable composition, or as a self-curable material.

13 Claims, No Drawings

COMPOUND HAVING THERMALLY DISSOCIATABLE THIOACETAL SKELETON, PRECURSOR THEREOF, CURED PRODUCT THEREOF, AND COMPOSITION FOR THEIR PRODUCTION

TECHNICAL FIELD

This invention relates to a thermally dissociatable thioacetal compound which can be used as a curing agent for urethane curable composition or as a thermally dissociatable material; a hemi(thio)acetal ester which is a precursor for such compound; a thermally dissociatable cured product containing thioacetal skeleton as its crosslinking site; and a composition for producing such compound or such cured product.

BACKGROUND ART

Plastic materials have the history that they have been developed in order to obtain highly durable materials which are hardly decomposed, and ironically, such high durability is now the cause of waste pollution, and in particular plastic pollution. To be more specific, conventional crosslinked cured products are not intended for chemical dissociation.

For example, a polysulfide polymer containing two or more thiol groups in the molecule is widely employed in sealants, coating compositions, adhesives and the like since such polysulfide polymer is capable of reacting with an epoxy, isocyanate, or the like which readily reacts with the thiol group to form a cured product with an increased molecular weight. A composition comprising a compound having hydroxyl group and a compound having two or more vinyl ether (enol ether) groups is also disclosed (EP 296507 A2), and this composition is claimed to be a curable composition which is free from substances that are toxic to human body such as an isocyanate or an aldehyde, which is safe since no toxic substance is discharged from the system, and which can be cured at a relatively low temperature into a product exhibiting excellent chemical and physical performance. These cured product, however, can not be softened or liquefied by chemical decomposition at the desired timing. With regard to the polysulfide polymer as mentioned above, cured product can be formed by using a metal oxide for the catalyst. However, the cured product is preferably free from such metal oxide in view of the safety and since inclusion of such metal oxide will necessitate further separation process.

Lately, there is a growing concern for protection of global environment including the problem of the waste pollution as mentioned above, and guidelines have been published to promote recycling by conducting the waste disposal in each industry or by item, for example, home appliance, OA equipment, and other commodities which enable efficient use of the resources. In correspondence with such situation, a strong demand exists for environmentally friendly materials which can be produced into recyclable products.

Biodegradable and photodegradable plastic materials have been developed in view of such situation. However, plastic materials should, on the other hand, perpetually retain its performance under normal conditions of use without undergoing degradation by decomposition or the like. Accordingly, there is an expectation for development of a thermally dissociatable material which thermally dissociates under temperature conditions which are different from the conditions of use and becomes liquefied or softened to enable disassembly of the structure to which this material has been adhered, and which, on the other hand, does not become degraded by decomposition while it is in use and retains its integrated (cured) conditions.

Conventional thermal dissociation technologies that have been known in the art include use of thermal dissociation in blocking technology of a curing system, and latent catalysts which become active by heat, light, moisture, oxygen, or other external stimulation, and blocking of functional group such as isocyanate group have been developed and put into practical use. For example, JP 4-175375 A discloses a one part thermosetting composition which is a composition comprising a hydroxyl group-containing compound and a vinyl ether group-containing compound further comprising a thermally latent acid catalyst.

JP 4-72324 A discloses a blocking technology of carboxyl group wherein carboxyl group in a thermosetting resin composition comprising a multifunctional vinyl (thio)ether compound having two or more vinyl (thio)ether groups and a compound having two or more carboxyl groups is blocked by monovinyl (thio)ether to form a hemi(thio)acetal ester group. However, the curing system utilizing such conventional blocking technology generally suffers from the problem after its curing that the component which is not involved in the reaction, for example, the blocking agent (protective group) either remains in the system or is discharged from the system in the thermal dissociation of the blocked compound, and such components results in the tack, toxicity, or contamination of the global environment.

Furthermore, the curing systems using the conventional blocking technology are silent about the thermal dissociation ability of the cured product obtained by such curing system.

DISCLOSURE OF THE INVENTION

An object of the present invention is to widely provide a thermally dissociatable material which is a curable material adapted for use as a sealant, coating material, adhesive or the like, and at the same time, which is thermally dissociatable at a temperature below the thermal decomposition temperature to enable disassembly of the material to which the thermally dissociatable material had been attached, and in some cases, recycling of the material. Such thermally dissociatable material is useful as a curing agent or a self-curable material, and also, believed to be useful as a thermal recording material or a heat storage material which stores heat by heat budget.

The inventors of the present invention made an intensive study to obviate the problems as described above, and found that, a thioacetal group wherein oxygen atom in the acetal group has been mono- or di-thiosubstituted (herein also referred to as a thioacetal group for the purpose of abbreviation) is thermally dissociatable. To be more specific, the inventors synthesized a compound having a thioacetal group (skeleton) in expectation of the thermal dissociation ability of the thioacetal group, and confirmed that heating of the thus synthesized compound results in the generation of vinyl (thio)ether and thiol. The thermal dissociation ability of the thioacetal group was thus found. The inventors also found that, when such thermally dissociatable thioacetal group is synthesized by the reaction between vinyl (thio)ether group and thiol group, there are cases when ether-type addition group is formed from the same starting materials, and such ether-type addition group does not exhibit thermal dissociation ability.

It was also confirmed that the compound having thioacetal skeleton as described above is well adapted for use as a thermally dissociatable material such as a self-curable product or a curing agent for a urethane curable composition. Both the curable composition wherein vinyl (thio)ether group is reacted with thiol group for curing, and the cured product of such curable composition are unknown.

The inventors also found that a thiol having hemi(thio) acetal ester skeleton undergoes intramolecular exchange reaction between the ester bonded carbonyloxy group and the thiol group to form thermally dissociatable thioacetal group, namely, that a thiol having hemi(thio)acetal ester skeleton is a precursor for a carboxylic acid having thioacetal skeleton. It should also be noted that, in such a case, the thioacetal skeleton is generated by the intramolecular exchange reaction in contrast to the case of conventional carboxylic acid-blocking technology, and no unnecessary compound such as blocking agent (protective group) is generated through the formation of the skeleton. In addition, the terminal thiol which requires addition of an amine in the reaction with epoxy can react with the epoxy with no addition of such amine if carboxylic acid is present on its terminal. Accordingly, the inventors found that, if a thiol having hemi(thio)acetal ester skeleton were mixed with epoxy, a cured product can be obtained with no addition of amine by heating to the curing temperature.

In view of such situation, the inventors estimated that, if a cured product has thioacetal skeleton incorporated therein, or if a composition containing hemi(thio)acetal ester which can generate thioacetal skeleton in the curing is cured, the cured product should be thermally dissociatable, and confirmed that the cured product was at least softened by heating. The inventors were then convinced that the cured product was thermally dissociatable. It was then found that a structure which is prepared by using such cured product, for example, as an adhesive can be readily disassembled by heating the structure to a temperature below the thermal decomposition temperature, and the present invention as described below was thereby completed. In view of such situation, (1) The present invention provides a thioacetal compound having a thermally dissociatable monothioacetal and/or dithioacetal skeleton.
(2) As an embodiment of such thioacetal compound, the present invention provides a thioacetal compound wherein the molecule has at least two terminal groups independently selected from hydroxyl group, thiol group, and carboxyl group. Such thioacetal compound is adapted for use as a crosslinkable compound (curing agent).
(3) The thioacetal compound may be a chain polymer wherein the monothioacetal and/or dithioacetal skeleton is included in the repeating unit.
(4) A typical example of such thioacetal compound is the one represented by the following formula (1):

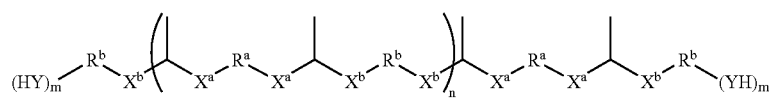

In the formula, $R^a$ and $R^b$ are independently an aliphatic hydrocarbon group containing 2 to 18 carbon atoms, an alkyl aromatic group containing 7 to 24 carbon atoms, or an aromatic group or a heterocyclic group containing 6 to 18 carbon atoms, said groups optionally containing a substituent or a hetero atom;

n is an integer of 0 to 10;

m is independently an integer of 1 to 3; and at least one of $X^a$ and $X^b$ is S, and the remainder are S or O, and YH is SH or OH.

(5) This invention also provides a hemi(thio)acetal ester represented by the following formula (2):

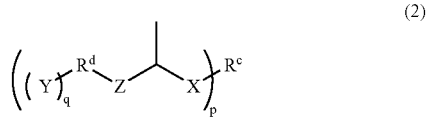

In the formula, $R^e$ and $R^d$ are independently an optionally substituted aliphatic hydrocarbon group, aromatic group, alkyl aromatic group, or heterocyclic group containing 2 to 24 carbon atoms, said group optionally containing at least one hetero atom selected from O, S, and N;

p is 1, 2, 3, or 4; and q is 1, 2, or 3;

X is S or O, and each X may be the same or different when p is 2 or more;

Y is SH, OH, or COOH, and each Y may be the same or different when p or q is 2 or more (provided that at least one of Y is SH or OH, and when Y is COOH, only one Y is COOH); and Z is COO, S, or O, and each Z may be the same or different when p is 2 or more provided that at least one of Y—$R^d$-Z- is HS—$R^d$—COO— or HO—$R^d$—COO—.

(6) A hemi(thio)acetal ester wherein at least one of Y—$R^d$-Z- is HS—$R^d$—COO— in the above formula, and thioacetal skeleton is generated by intramolecular exchange reaction between the SH group and the COO is provided as a precursor for the thioacetal compound of any one of the above (1) to (4).

(7) The present invention also provides a crosslinked cured thioacetal which contains at least one thermally dissociatable monothioacetal and/or dithioacetal skeleton as its site of crosslinking.

(8) Such thioacetal compound, hemi(thio)acetal ester, or crosslinked cured thioacetal is a derivative of a vinyl ether or a vinyl thioether (A) (which may be herein abbreviated as a vinyl(thio)ether) having vinyl ether and/or vinyl thioether terminal group.

(9) Accordingly, the present invention provides a composition for producing such thioacetal compound wherein the composition comprises (A) a vinyl (thio)ether compound having at least one vinyl ether and/or vinyl thioether terminal group; and (B) a thiol compound having at least one thiol group.

(10) The present invention also provides a curable composition comprising (A) a multifunctional vinyl (thio)ether compound having two or more vinyl ether and/or vinyl thioether terminal groups; and (B) a thiol compound having at least one thiol group.

This curable composition is a composition adapted for use in producing the crosslinked cured thioacetal as described in the above (7). Both (A) and (B) may preferably contain two or more of the above-described particular substituents. Furthermore, when at least one of (A) and (B) contains 3 or more of the above-described particular substituent, production of a self-crosslinked cured product will be enabled.

(11) In each of the composition as described above, when the compound (B) is an aromatic thiol, thioacetal group which is not ether type can be formed through the reaction with the vinyl (thio)ether compound without coexistence of an acid catalyst as described below, and this is preferable.

(12) When each of the composition as described above further comprises an acid catalyst (C), thioacetal group can be formed even if the compound (B) were not an aromatic thiol.

Preferable examples of the acid catalyst (C) are acidic phosphates.

(13) The present invention also provides a curable composition comprising the thioacetal compound of any one of the above (1) to (4), and for example, a curable composition comprising the thioacetal compound, and a multifunctional compound which is capable of reacting with hydroxyl group, thiol group or carboxyl group.

Such thioacetal compound is preferably a compound which has hydroxyl or thiol terminal group, and the multifunctional compound reactive with such terminal group is preferably urethane prepolymers having terminal isocyanate group.

(14) The hemi(thio)acetal ester of the above (5) or (6) forms a carboxylic acid having the thioacetal skeleton by intramolecular exchange reaction. Therefore, this invention also provides a curable composition comprising such hemi(thio)acetal ester and a multifunctional compound having a group capable of reacting with carboxyl group. The multifunctional compound is preferably a high molecular weight compound which has a group capable of reacting with carboxyl group. Exemplary preferable such high molecular weight compounds include epoxy resins and high molecular weight compounds having carbonate group, oxazolidine group, ester group, maleic group, silanol group, or the like.

(15) This invention also provides a thermally dissociatable cured product which is produced by crosslinking and curing each of the curable composition.

(16) In the thioacetal compound, crosslinked cured thioacetal, or thermally dissociatable cured product of the present invention, the thioacetal group thermally dissociates into thiol group and vinyl ether group and/or vinyl thioether group.

BEST MODE FOR CARRYING OUT THE INVENTION

Next, the present invention is described in further detail.

The thioacetal compound of the present invention is a compound which has at least one monothioacetal and/or dithioacetal skeleton (group) represented by the following structural formulae in the molecule.

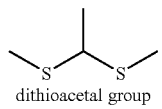
dithioacetal group

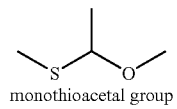
monothioacetal group

The thioacetal group dissociates into thiol group and vinyl ether group or vinyl thioether group by heating. This dissociation will be illustratively demonstrated in this specification in the Experiment 1.

This invention provides a thermally dissociatable material which utilizes such thermal dissociation of the thioacetal group, and examples of such thermally dissociatable material include an uncured thioacetal compound such as compound (1) as will be described below, a crosslinked cured thioacetal containing at least one thioacetal skeleton as its site of crosslinking, a cured thioacetal compound formed by self-crosslinking of the thioacetal compound, a hemi(thio)acetal ester which may serve a precursor for the thioacetal compound (see compound (2) as will be described below), a curable composition containing a thioacetal compound, a curable composition containing a hemi(thio)acetal ester, and a thermally dissociatable cured product produced by crosslinking and curing such curable composition.

The thioacetal compound, the hemi(thio)acetal ester, and the crosslinked cured thioacetal as mentioned above are derivatives of a vinyl (thio)ether compound (A) having vinyl ether and/or vinyl thioether terminal group.

First, a composition containing the vinyl (thio)ether compound (A) which may be used for producing the thioacetal compound having thioacetal skeleton, or the cured product formed by self-crosslinking wherein thioacetal skeleton is used for the crosslinking site is described.

The vinyl (thio)ether compound (A) incorporated in the composition is a compound having a vinyl ether group and/or a vinyl thioether group represented by the following general formula on its terminal, and preferably, a compound having two or more vinyl (thio)ether terminal groups in one molecule.

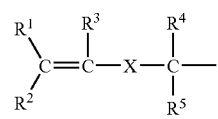

In the formula, $R^1$, $R^2$, $R^3$, $R^4$, and $R^5$ are independently hydrogen atom or an organic group containing 1 to 16 carbon atoms, and $R^1$ or $R^2$ together with $R^4$ or $R^5$ may form a heterocycle. X is oxygen atom or sulfur atom.

$R^1$ to $R^5$ are preferably hydrogen atom or a lower alkyl group such as methyl group, ethyl group, or propyl group, and more preferably, hydrogen atom.

The organic group used herein is an alkyl group, a cycloalkyl group, or an aryl group which is optionally substituted with at least one group selected from the group consisting of a cycloalkyl group, an alkoxyl group, a cycloalkoxy group, an aryl group, an aryloxy group, an alkanoyloxy group, an aralkyloxy group and a halogen atom.

The vinyl (thio)ether compound (A) is not limited whether it is a low molecular weight compound (containing divinyl ether monomer) or a high molecular weight compound (containing vinyl ether-terminated prepolymer). Exemplary vinyl (thio)ether compounds (A) are the compounds as described below.

(a) ethylene glycol divinyl ether, propylene glycol divinyl ether, diethylene glycol divinyl ether, triethylene glycol divinyl ether, tetraethylene glycol divinyl ether, butanediol divinyl ether, butanediol diisopropenyl ether, pentanediol divinyl ether, hexanediol divinyl ether, neopentyl glycol diisopropenyl ether, trimethylolpropane trivinyl ether, pentaerythritol tetravinyl ether, cyclohexanediol divinyl ether, cyclohexanedimethanol divinyl ether, 2,2-bis[p-(2-vinyloxyethoxy)phenyl]propane, Shichichenko ester of acrolein dimer, and other low molecular weight, multifunctional vinyl ethers; and the low molecular weight multifunctional vinyl thioethers corresponding to such low molecular weight, multifunctional vinyl ethers.

(b) addition products of a low molecular weight, multifunctional vinyl ether or a low molecular weight, multifunctional vinyl thioether and a polyol, for example, addition products of the low molecular weight, multifunctional vinyl ether or the low molecular weight, multifunctional vinyl thioether (a) with a polyol such as ethanediol, propanediol, butanediol, pentanediol, octanediol, an analog thereof, or a corresponding oligomeric ether; glycerine, trimethylolethane, trimethylolpropane, hexanetriol, pentaerythritol, dipentaerythritol, sorbitol, polyvinylalcohol, bisphenol A, resorcin, hydroquinone, or a derivative thereof; trishydroxyethyl isocyanurate; hydroxyl group-containing epoxide; hydroxyl group-containing polyether; hydroxyl group-containing polyester; hydroxyl group-containing polyacryl; or the like.

Molecular weight of the backbone when the vinyl (thio)ether compound (A) is a high molecular weight compound is not particularly limited, and any desired molecular weight may be selected depending on the performance and the intended use of the composition.

It is also to be noted that such vinyl (thio)ether compound may be used either alone or in combination of two or more. When two or more vinyl (thio)ether compounds are used, the compounds may be mixed at any ratio depending on the performance and the intended use of the composition.

The thiol compound (B) incorporated in the composition of the present invention may be preferably a polythiol which contains two or more thiol groups in the molecule. Exemplary such polythiol compounds include 1,3-butanedithiol, 1,4-butanedithiol, 2,3-butanedithiol, 1,2-benzenedithiol, 1,3-benzenedithiol, 1,4-benzenedithiol, 1,10-decanedithiol, 1,2-ethanedithiol, 1,6-hexanedithiol, 1,9-nonanedithiol, 1,8-octanedithiol, 1,5-pentanedithiol, 1,2-propanedithiol, 1,3-propanedithiol, toluene-3,4-dithiol, 3,6-dichloro-1,2-benzenedithiol, 1,3,5-triazine-2,4,6-trithiol (trimercapto-triazine), 1,5-naphthalenedithiol, 1,2-benzenedimethanethiol, 1,3-benzenedimethanethiol, 1,4-benzenedimethanethiol, 4,4'-thiobisbenzenethiol, 2-di-n-butylamino-4,6-dimercapto-s-triazine, trimethylolpropantris (β-thiopropionate), 2,5-dimercapto-1,3,4-thiadiazole, 1,8-dimercapto-3,6-dioxaoctane, and 1,5-dimercapto-3-thiapentane.

Among these, trimercapto-triazine and 2-di-n-butylamino-45,6-dimercapto-s-triazine are preferable for use in the curable composition of the present invention since they are solid and odorless and therefore easy to handle, and since they exhibit high curing speed as well as excellent adhesion to metals.

The polythiol (B) may also be a polysulfide polythiol. The "polysulfide" used herein generally designates a poly-mercapto compound having the structure wherein two or more hydrogen atoms of a hydrocarbon has been substituted with mercapto group. Typical such polysulfide polythiols are those wherein the polymer skeleton moiety has the structure of polyether, polythioether, polyester, acryl copolymer, urethane copolymer, polyacetal, polybutadiene, polyisoprene, polyolefin, polychloroprene, polysulfide, or a copolymer thereof.

Use of the polysulfide polymer and polysulfide polyether polymer are particularly preferable since they are advantageous in making use of the thermal dissociation ability. With regard to the position of the thiol group, thiol group is preferably located at the terminal of the molecule's backbone although the position is not particularly limited.

The polysulfide polythiol used may generally have a number average molecular weight of approximately 500 to 100000, and preferably approximately 500 to 10000.

The polythiol used in the present invention is preferably a polythiol having an average SH number of 5.45 and an SH equivalent of 218 (product name, Thiokol LP70, manufactured by Toray Thiokol; Structure: HS–(CH$_2$CH$_2$OCH$_2$OCH$_2$CH$_2$—S$_2$–)$_n$CH$_2$CH$_2$OCH$_2$OCH$_2$CH$_2$—SH) since this polythiol has a high average SH number. The "SH number" used herein designates the number of functional groups (the number of thiol groups) per one molecule of the polythiol, and the "SH equivalent" used herein designates the molecular weight per one thiol group.

In the present invention, use of a compound having an aromatic thiol group (aromatic thiol) for the thiol compound (B) is particularly preferable, since a thermally dissociatable compound having thioacetal skeleton can be produced by the reaction with the vinyl (thio)ether without using an acid catalyst.

Examples of the aromatic thiol include trimercapto-triazine, 2-di-n-butylamino-4,6-dimercapto-s-triazine, 1,3-benzenedithiol, and 4,4'-thiobisbenzenethiol, and among these, trimercapto-triazine is preferable since this compound is odorless. The curable composition of the present invention may contain an acid catalyst (C). Exemplary acid catalysts include protonic acids such as HCl, H$_2$SO$_4$, H$_2$PO$_4$, HBr, and HNO$_3$, Lewis acids such as ZnCl$_2$ and SnCl$_4$, organic tin compounds, and phosphates. Use of an acidic phosphate is preferable in view of the handling convenience.

The inventors of the present invention have found that, in the reaction of the vinyl (thio)ether compound (A) and the thiol compound (B) as described above, a branched (acetal type) skeleton is formed when the reaction is allowed to take place in the presence of an acid catalyst (C) (as shown by the reaction formula (ii), below), or when the reaction is allowed to proceed by using an aromatic thiol compound of the thiol compound (B) (as shown by the reaction formula (iii), below), while a linear (ether type) skeleton is formed when the reaction is allowed to proceed by using a thiol compound (B) which is not an aromatic thiol compound in the absence of a catalyst (as shown in reaction formula (i), below). The acetal type thioacetal group undergoes thermal dissociation while the skeleton is not thermally dissociatable in the case when an ether type thioether is formed.

Next, embodiments wherein difunctional compounds are used for both compounds (A) and (B) to produce a linear thioacetal compound are shown. To be more specific, the divinyl ether (A) used was cyclohexanedimethanol divinyl ether and the dithiol (B) used was 1,8-dimercapto-3,6-dioxaoctane (reaction formulae (i) and (ii)) or triazine compound (reaction formula (iii)).

Reaction formula (i) is directed to an embodiment wherein a linear (ether type) skeleton is obtained without using any acid catalyst.

Reaction formula (ii) is directed to an embodiment wherein a branched (acetal type) skeleton is obtained in the presence of an acid catalyst.

Reaction formula (iii) is directed to an embodiment wherein a branched (acetal type) skeleton is obtained without using any acid catalyst by using an aromatic thiol compound.

It should be noted that "r.t." designates room temperature in the following reaction formula.

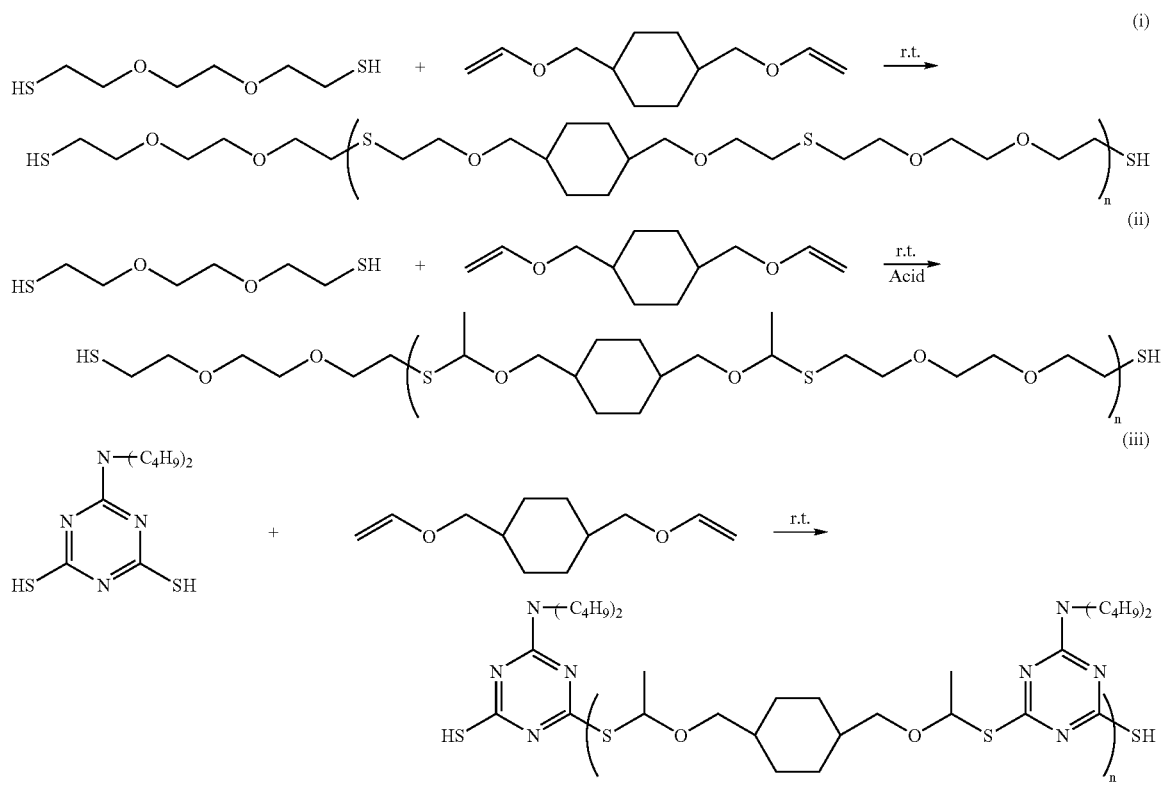

In the above reaction formulae (i) to (iii), the vinyl (thio)ether compound (A) and the thiol compound (B) are preferably used such that the molar ratio (vinyl ether group/thiol group) of the vinyl ether group in (A) to the thiol group in (B) is 0.5 to 1, preferably 0.5 to 0.8, and more preferably 0.6.

In addition, in the reaction formula (ii), the acid catalyst (C) is preferably used at an amount of 0.5 to 20% by mole, preferably 0.5 to 10% by mole, and more preferably 1.0% by mole or 0.01% by weight in relation to the total amount of vinyl (thio)ether compound (A) and thiol compound (B).

The thioacetal compound of the present invention may be a polymer (including oligomer) produced from the composition comprising (A) and (B), which includes the thioacetal skeleton as its repeating unit. The thioacetal compound of the present invention may also be a chain polymer of such acetal compound with another difunctional compound. Such chain polymer may also be used as a thermally dissociatable material (plastic material).

<Self-Crosslinking Composition>

In the present invention, a cured product that had cured by the crosslinking reaction between the vinyl (thio)ether (A) and thiol (B) can be formed from the composition for forming thioacetal skeleton as described above, and the present invention provides a first curable composition which can be used to form such cured product. Such crosslinked cured thioacetal is one of the thermally dissociatable materials of the present invention, and therefore both (A) and (B) may preferably contain two or more of the above-described particular groups, namely, two or more vinyl (thio)ether groups and two or more thiol group, respectively. Furthermore, when at least one of (A) and (B) contains three or more of the above-described particular substituent, production of a self-crosslinked cured product will be enabled.

Accordingly, the curable composition may further comprise an acid catalyst (C) for the purpose of producing a thermally dissociatable cured product.

Such curable composition can be cured at room temperature to 150° C. for 15 minutes to 180 minutes to thereby produce the cured product. The curing temperature is preferably 80 to 120° C., and more preferably 100° C. Curing time is preferably 15 minutes to 120 minutes, and more preferably 15 minutes to 60 minutes.

In contrast to the ether type cure product which does not thermally dissociate by re-heating, the acetal type cured product produced in the above-described process can be softened or liquefied by re-heating to a higher temperature and preferably, by re-heating to 150 to 180° C. for thermal dissociation whereby intramolecular cleavage takes place. This process will be demonstrated in the Examples, below, and as a result of such thermal dissociation, the product will be ready for disassembly.

Furthermore, as will be demonstrated in the Examples, when an aromatic thiol is used for the component (B) in the curable composition, the thermal dissociation temperature can be reduced by incorporating acid catalyst (C).

The thermal dissociation time is preferably 1 minute to 60 minutes, and more preferably 1 minute to 30 minutes.

When the curable composition as describe above is produced into a sealant or an adhesive composition, the curable composition of the present invention may be blended with an inorganic filler or a plasticizer.

The inorganic filler is blended for the purpose of reducing the cost, improving physical properties, and adjusting viscosity. The type and the amount of the inorganic filler used should be carefully determined since activity, particle shape, pH, surface treatment, and the like of the filler greatly affects isocyanate group, and hence, the storage stability, curing speed, physical properties, and foaming. The inorganic fillers commonly used include calcium carbonate, talk, silica, and carbon black. The plasticizer is blended to adjust viscosity and physical properties. Any placticizer which is inactive with the isocyanate group, and which is compatible and bleed-free may be used. The plasticizer commonly used include dioctyl phthalate, dibutyl phthalate, and dioctyl adipate.

A sealant containing the curable composition can be used as a sealant for building materials and double glazing.

In addition to the critical components as described above, the curable composition may further contain a curing catalyst, a filler other than those mentioned above, a thixotropic agent, a pigment, a dye, an antiaging agent, an antioxidant, an antistatic agent, a flame retardant, a tackifier, a dispersing agent, a solvent, or the like at an amount which does not adversely affect the merits of the present invention.

<Uncured Thioacetal Compound>

An embodiment of the thioacetal compound of the present invention is uncured thioacetal compound having at least two terminal groups which are respectively selected from hydroxyl group, thiol group, and carboxyl group. Such thioacetal compound can be used as a crosslinkable compound (curing agent). Such thioacetal compound may be a chain polymer including the above-described thioacetal skeleton in the repeating unit.

As typical such thioacetal compound, the present invention provides a compound represented by the following formula (1) (the compound is hereinafter also referred to as compound (1)).

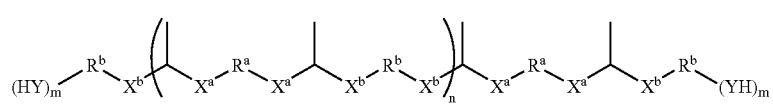

(1)

In the formula, $R^a$ and $R^b$ are independently an aliphatic hydrocarbon group containing 2 to 18 carbon atoms, an alkyl aromatic group containing 7 to 24 carbon atoms, or an aromatic group or a heterocyclic group containing 4 to 18 carbon atoms, said group optionally containing a substituent or a hetero atom;

n is an integer of 0 to 10;

m is independently an integer of 1 to 3; and at least one of $X^a$ and $X^b$ is S, and the remainder are S or O, and YH is SH or OH.

When $R^a$ and $R^b$ are aliphatic hydrocarbon group in the above formula, the aliphatic hydrocarbon group may be either linear or branched, and either a saturated hydrocarbon group or an unsaturated hydrocarbon group. Exemplary alkyl aromatic groups include benzyl group, phenetyl group, xylylene group, and 4,4'-isopropylidenediphenyl; exemplary aromatic groups include phenylene group and naphthylene group; and exemplary heterocyclic groups include triazine group, and 1,3,4-thiadiazole group. Exemplary substituents include halogen atoms such as fluorine atom and chlorine atom, an ester, an aldehyde, and an ether. Exemplary hetero atoms include oxygen atom, sulfur atom, and nitrogen atom.

At least one of $X^a$ and $X^b$ are S, and the monothioacetal skeleton or the dithioacetal skeleton as described above is thereby formed.

Compound (1) has at least one such thioacetal group in its molecule, and the compound is thereby imparted with thermal dissociation ability.

Next, compound (1) is described in further detail depending on the number of n in the above formula.

[When n is 0]

When n is 0, compound (1) is represented by the following formula (1-1) (this compound is hereinafter also referred to as compound (1-1)).

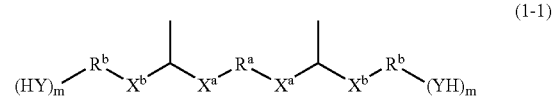

(1-1)

In the formula, symbols are as defined above for the formula (1).

In the formula, $R^a$ and $R^b$ may represent an alkylene group such as methylene group, ethylene group, trimethylene group, propylene group, and cyclohexanedimethylene group; an alkoxyalkylene group such as oxyalkylene group; an alkyl aromatic group such as xylylene group and isopropylidenediphenyl; an aromatic group such as phenylene group and naphthylene group; or a heterocyclic group such as triazine group and 1,3,4-thiadiazole group. Among these, $R^a$ is preferably xylylene group, cyclohexanedimethylene group, or oxyalkylene group, and $R^b$ is preferably methylene group, ethylene group, dioxaoctylene group, oxyalkylene group, phenylene group, or triazine group.

At least one of $X^a$ and $X^b$ is S, and preferably, at least one of $X^b$ is S. $X^a$ is preferably O in view of the ease of obtaining the starting material.

Compound (1-1) is a compound which has at least one of dithioacetal group and monothioacetal group in the molecule. The type and the number of these groups may be adequately selected depending on the properties desired for the compound. For example, when the dissociation at a high speed is desired, the compound preferably includes one or more dithioacetal group, or alternatively, 2 to 4 thioacetal groups, and when the dissociation at a high temperature is desired, the compound may preferably include one monothioacetal group.

The number of Y is preferably 1 in view of ease of reaction control, and therefore, m is preferably 1.

[When n is 1 to 10]

When n is 1 to 10, compound (1) is represented by the following formula (1-2) (this compound is hereinafter also referred to as compound (1-2)).

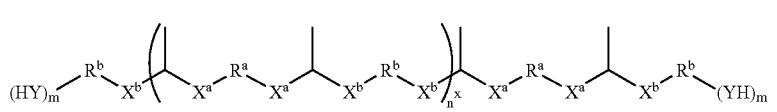

(1-2)

In the formula, $n^x$ is an integer of 1 to 10, and other symbols are as defined above for the compound (1). The preferable embodiments of $R^a$, $R^b$, $X^a$, $X^b$, Y, and m are as defined for the compound (1-1), and compound (1-2) is also a compound which has at least one dithioacetal group or monothioacetal group in the molecule.

Of the groups represented by the formula: [—$X^a$—CH(CH$_3$)—$X^b$—], content of dithioacetal group is preferably 1 to 100%, more preferably 5 to 90%, and most preferably 10 to 80%. The content of the monothioacetal group is preferably 3 to 100%, more preferably 10 to 90%, and most preferably 20 to 80%.

Total content of the dithioacetal group and the monothioacetal group are preferably 1 to 100%, more preferably 5 to 100%, and most preferably 10 to 100%.

A preferred embodiment of the compound (1) is the compound having cyclohexyl skeleton represented by the following formula.

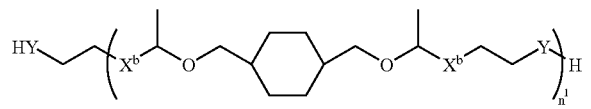

In the formula, $X^b$ and Y are independently O or S (provided that at least one of $X^b$ is S), and $n^1$ is an integer of 1 to 3.

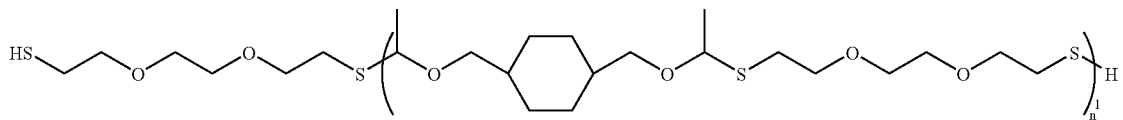

In the formula, $n^1$ is an integer of 1 to 3.

The compound (1) as described above may be synthesized by using a compound which has two or more vinyl ether groups in the molecule and a compound which has two or more thiol groups in the molecule or a compound which has one or more thiol group and one or more hydroxyl group in the molecule for the starting materials. These materials used for the synthesis are as described above for the curable composition, namely, for the compound (A) having vinyl (thio)ether group and the compound (B) having thiol group, respectively, and further description is omitted to avoid redundancy.

Accordingly, this invention also provides a composition for producing the above-described thioacetal compound which is preferably compound (1), comprising a vinyl (thio)ether compound (A) having at least one vinyl ether and/or vinyl thioether terminal group; a thiol compound (B) having at least one thiol group; and optionally, an acid catalyst (C).

Among these, compound (1) can be synthesized by reacting the starting materials as described above in the presence of an acid catalyst such as a phosphate, a Lewis acid, or hydrochloric acid at room temperature. The compound synthesized by such method is a mixture of compounds (1) wherein n is an integer of 1 to 10. Average value of n is preferably 1 to 10, more preferably 2 to 10, and still more preferably 3 to 10. Average value of n can be adjusted to the desired range by selecting the reactants of adequate equivalent.

As described above, the compound (1) of the present invention has thermally dissociatable dithioacetal group and/or monothioacetal group in the molecule, and therefore, when the compound (1) is used as a curing agent in the curable composition, the cured product can be readily disassembled after curing by heating to a temperature below the thermal decomposition temperature of the cured product.

The compound (1) as described above may be used in forming a curable composition with a resin which has a group capable of crosslinking with said compound. In such a case, the compound (1) may be adequately selected from those described above depending on the intended use of the composition.

<Second Curable Composition>

The present invention also provides a second curable composition which contains the thioacetal compounds (1) to (4) as described above, for example, a curable composition which contains such thioacetal compound and a multifunctional compound reactive with hydroxyl group, thiol group, or carboxyl group.

The thioacetal compound is a compound which has hydroxyl or thiol terminal group, and the multifunctional compound reactive with such terminal group is a resin which has a group that is capable of crosslinking with the compound (1). Such resin is not particularly limited as long as it is a resin which has a group capable of crosslinking with terminal thiol or hydroxyl group of the compound (1). Exemplary such resins include urethane prepolymers having terminal isocyanate group, and resins having epoxy, vinyl, or maleic group.

The urethane polymer which may be used in the composition of the present invention is a reaction product obtained by reacting a polyol compound with an excessive amount of polyisocyanate compound (namely, by reacting OH group with an excessive amount of NCO group), and the urethane polymer may generally have 0.5 to 30% by mass of isocyanate group at the terminal of the molecule.

Exemplary polyisocyanate compounds which may be used for producing such urethane polymer include aromatic ring-containing polyisocyanates such as 2,4-tolylene diisocyanate (2,4-TDI), 2,6-tolylene diisocyanate (2,6-TDI), 4,4'-diphenylmethane diisocyanate (4,4'-MDI), 2,4'-diphenylmethane diisocyanate (2,4'-MDI), p-phenylene diisocyanate, polymethylene polyphenylene polyisocyanate, xylylene diisocyanate (XDI), tetramethylxylylene diisocyanate (TMXDI), and 1,5-naphthalene diisocyanate (NDI); aliphatic polyisocyanates such as tolidine diisocyanate (TODI) and hexamethylene diisocyanate (HDI); alicyclic polyisocyanates such as isophorone diisocyanate, $H_6XDI$ (hydrogenated XDI), and $H_{12}MDI$ (hydrogenated MDI); and polyisocyanates which are the carbodiimide-modified products or isocyanurate-modified products of the above-mentioned polyisocyanates, which may be used alone or in combination of two or more.

The polyol compound which may be used in the present invention include polyether polyols, polyester polyols, other polyols, and mixtures of such polyols. Exemplary polyether polyols include dihydric alcohols such as ethylene glycol, diethylene glycol, propylene glycol, dipropylene glycol, 1,3-butanediol, 1,4-butanediol, 4,4'-dihydroxy phenylpropane, and 4,4'-dihydroxyphenylmethane; polyhydric alcohols such as glycerine, 1,1,1-trimethylolpropane, 1,2,5-hexanetriol, and pentaerythritol; diamines such as ethylenediamine and aromatic diamine; polyols obtained by adding at least one alkylene oxide such as ethylene oxide, propylene oxide, butylene oxide, and stylene oxide to at least one sugar such as sorbitol; and polyoxytetramethylene oxide.

The polyester polyols are roughly categorized into condensed polyester polyol, lactone polyol, and polycarbonate diols, and exemplary polyester polyols include condensed polymer of one or more of ethylene glycol, propylene glycol, butanediol, pentanediol, hexanediol, cyclohexanedimethanol, glycerine, 1,1,1-trimethylolpropane, and other low molecular weight polyols with one or more of glutaric acid, adipic acid, pimelic acid, suberic acid, sebacic acid, terephthalic acid, isophthalic acid, dimer acid, and other low molecular weight carboxylic acids or oligomer acids; and ring-opened polymers of propionlactone, valerolactone, or the like.

Exemplary other polyols include polyols whose backbone comprises C—C bond, for example, acrylic polyol, polybutadiene polyol, and hydrogenated polybutadiene polyol, and low molecular weight polyols such as ethylene glycol, diethylene glycol, propylene glycol, dipropylene glycol, butanediol, pentanediol, and hexanediol.

In the production of the urethane polymer having terminal isocyanate group from the polyisocyanate compound and the polyol compound as described above, the polyol compound and the polyisocyanate compound are generally mixed at a ratio such that, 1.2 to 3 equivalents (NCO equivalent), and preferably 1.2 to 2 equivalents of the polyisocyanate compound is used per 1 equivalent (OH equivalent) of the polyol compound. Such urethane polymer is synthesized by mixing the two compounds at the predetermined ratio and heating the mixture to a temperature of 30 to 120° C., and preferably 50 to 100° C. with stirring.

In the composition of the present invention, content of the compound (1) is preferably 1 to 150 parts by mass, more preferably 3 to 150 parts by mass, and still more preferably 10 to 120 parts by mass per 100 parts by mass of the resin. Content of less than 3 parts by mass is undesirable since thermal dissociation is less likely to take place in the resulting product, and content in excess of 150 parts by mass is undesirable since the compound (1) is likely to remain partly unreacted.

In addition to the compound (1) and the resin having a group which is capable of crosslinking with the compound (1), the composition of the present invention may contain a filler, a curing aid, an antiaging agent, a solvent, a plasticizer, or other additives at an amount which does not adversely affect the merit of the present invention.

The filler may be an organic or an inorganic filler of varying shape, and exemplary fillers include fumed silica, calcined silica, precipitated silica, pulverized silica, melted silica; diatomaceous earth; iron oxide, zinc oxide, titanium oxide, barium oxide, magnesium oxide; calcium carbonate, magnesium carbonate, zinc carbonate; pyrophyllite clay, kaolin clay, calcined clay; carbon black; and any of the foregoing treated with a fatty acid, a resin acid, or a fatty acid ester. In the composition of the present invention, the filler is preferably used at a content of 1 to 200 parts by mass, and more preferably 1 to 100 parts by mass per 100 parts by mass of the resin.

Exemplary curing aids include N-β(aminoethyl)γ-aminopropyltrimethoxysilane, chloropropyltrimethoxysilane, vinyltrichlorosilane, γ-aminopropyltriethoxysilane, γ-mercaptopropyltrimethoxysilane, γ-methacryloxypropyltrimethoxysilane, and other silane coupling agents, among which aminosilane coupling agent being the preferred. In the composition of the present invention, content of the curing aid is preferably 1 to 20 parts by mass, and more preferably 1 to 10 parts by mass per 100 parts by mass of the resin.

Exemplary antiaging agents include N,N'-diphenyl-p-phenylenediamine (DPPD), N,N'-dinaphthyl-p-phenylenediamine (DNPD), 2,2,4-trimethyl-1,3-dihydroquinoline (TMDQ), and N-phenyl-1-naphthylamine (PAN). In the composition of the present invention, content of the antiaging agent is preferably 1 to 20 parts by mass, and more preferably 1 to 10 parts by mass per 100 parts by mass of the resin.

Exemplary solvents include acetone, methanol, ethanol, ethylether, gasoline, xylene, toluene, benzene, chloroform, ethyl acetate, and mineral spirits. In the composition of the present invention, content of the solvent is preferably 1 to 20 parts by mass, and more preferably 1 to 10 parts by mass per 100 parts by mass of the resin.

Exemplary plasticizers include dioctyl phthalate (DOP), dibutyl phthalate (DBP); dioctyl adipate, and isodecyl succinate; diethylene glycol dibenzoate, and pentaerythritol ester; butyl oleate, methyl acetylrecinoleate; tricresyl phosphate, trioctyl phosphate, and other phosphates; and polypropylene glycol adipate and polybutylene glycol adipate. In the composition of the present invention, content of the plasticizer is preferably 0.01 to 50 parts by mass, and more preferably 0.01 to 30 parts by mass per 100 parts by mass of the resin.

The composition can be produced by ordinary method employed in the art, namely, by mixing the compound (1), the resin having a group which is capable of crosslinking with the compound, and other additives, and thoroughly kneading the mixture preferably at a reduced pressure for uniform dispersion of the components.

The cured product produced by curing such composition will be softened or liquefied by heating to a temperature below the thermal decomposition temperature of the cured product, and the cured product can then be readily disassembled. In other words, the composition of the present invention is a composition which is capable of curing into a thermally dissociatable product.

The cured product may preferably have a thermal dissociation temperature of 100 to 250° C., preferably 100 to 200° C., and more preferably 150 to 200° C. When the cured product is dissociated at a temperature less than 100° C., the cured product can not be used for the application wherein the product is exposed to a high temperature, and when the cured product is not dissociated at a temperature in excess of 250° C., working efficiency will be poor and the resin itself will be decomposed with the risk of generating a toxic gas. The dissociation time is preferably 1 minute to 24 hours, more preferably 1 minute to 12 hours, and still more preferably 1 minute to 10 hours, and dissociation within such period is preferable in view of working efficiency and economy.

The thermal dissociation temperature and the dissociation time may be adequately selected depending on the intended use of the product by selecting the type of the compound (1).

The composition as described above is adapted for use as an adhesive or a sealant in construction and automobile applications.

The product produced by curing the composition of the present invention is thermally dissociatable, and therefore, when a members is adhered to another member or a reinforcement by using the composition of the present invention, the members or the member and the reinforcement can be readily disassembled by heating, and recycling of the member is thereby enabled contributing the maintenance of the global environment.

<Hemi(Thio)Acetal Ester>

This invention provides a compound having hemi(thio)acetal ester skeleton as a derivative of the vinyl (thio)ether (A), and to be more specific, a hemi(thio)acetal ester represented by the following formula (2) (hereinafter also referred to as compound (2)).

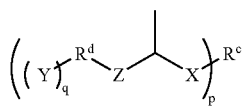

(2)

In the formula, $R^c$ and $R^d$ are independently an optionally substituted aliphatic hydrocarbon group, aromatic group, alkyl aromatic group, or heterocyclic group containing 2 to 24 carbon atoms, said groups optionally containing at least one hetero atom selected from O, S, and N;

p is 1, 2, 3, or 4; and q is 1, 2, or 3;

X is S or O, and X may be the same or different when p is 2 or more;

Y is SH, OH, or COOH, and Y may be the same or different when p or q is 2 or more (provided that at least one of Y is SH or OH, and when Y is COOH, only one Y is COOH); and Z is COO, S, or O, and Z may be the same or different when p is 2 or more provided that at least one of Y—$R^d$-Z- is HS—$R^d$—COO— or HO—$R^d$—COO—.

In the above compound, when at least one of Y—$R^d$-Z- is not HS—$R^d$—COO—, X is preferably S.

With regard to $R^c$ and $R^d$ in the above formula, the aliphatic hydrocarbon group may be either a straight-chain or branched linear hydrocarbon group, or an alicyclic hydrocarbon group; may contain a hetero atom such as O, S, or N; and may be either a saturated hydrocarbon group or an unsaturated hydrocarbon group. The aromatic group is preferably phenyl group, naphthyl group, or diphenyl group; the alkyl aromatic group is preferably xylylene group, 4,4'-isopropylidene diphenyl group, or diphenylmethane group; and the heterocyclic group is preferably triazine group, or 1,3,4-thiadiazol group. Exemplary substituents include halogens such as fluorine atom and chlorine atom, ethers, esters, amides, ketones, and aldehydes.

Next, compound (2) is described in further detail depending on the number of p in the formula.

[When p is 1]

When p is 1, the compound (2) is represented by the following formula (hereinafter also referred to as compound (2-1)).

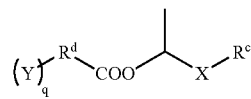

(2-1)

(In the formula, symbols are as defined above for the formula (2).)

$R^c$ is preferably an alkyl group such as methyl group, ethyl group, propyl group, isopropyl group, ethylhexyl group, butyl group, pentyl group, nonyl group, cyclohexyl group, stearyl group, or cyclohexanedimethyl group; an aromatic group such as phenyl group or naphthyl group; or a high molecular weight group such as a resin or a rubber.

$R^d$ is preferably an alkylene group, an oxyalkylene group, a phenylene group, or a naphthylene group corresponding to the above $R^c$, among which methylene group, ethylene group, phenylene group, naphthylene group, oxyethylene group, and the like being the preferred in particular.

q is preferably 1 in view of the ease of controlling the addition reaction, and in such case, Y is preferably SH.

X is preferably O in view of economy.

Compound (2-1a) represented by the following formula which has two or more hemiacetal ester structures or hemithioacetal ester structures is also a compound wherein a intramolecular exchange reaction may take place as in the case of compound (2).

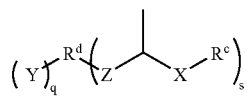

(2-1a)

In the formula, s is 2 or 3, and other symbols are as defined above for the formula (2).

[When p is 2]

When p is 2, the compound (2) is represented by the following formula (hereinafter also referred to as compound (2-2)).

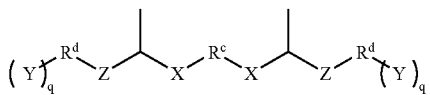

(2-2)

In the formula, symbols are as defined above for the formula (2).

$R^c$ is preferably an alkylene group, phenylene group, cyclohexylene group, an oxyalkylene group, or cyclohexanedimethylene group corresponding to those mentioned for the $R^c$ of the compound (2).

$R^d$ is preferably the same as those defined for compound (2).

q is preferably 1 in view of the ease of controlling the addition reaction.

X is preferably O in view of economy.

An embodiment wherein p is 2 is compound (2-2a) represented by the following formula:

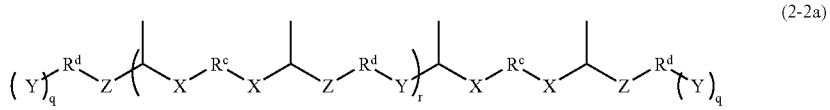

(2-2a)

In the formula, r is 1 to 5, and other symbols are as defined for compound (2)

[When p is 3]

When p is 3, the compound (2) is represented by the following formula (compound (2-3)).

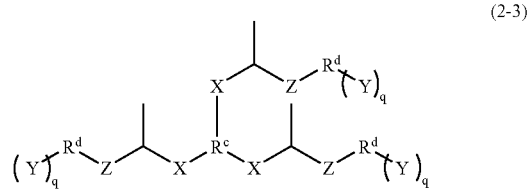

(2-3)

In the formula, symbols are as defined above for the formula (2).

$R^c$ is preferably a trivalent hydrocarbon group, phenyl group, cyclohexanedimethyl group, or trimethylolpropyl group corresponding to those mentioned for the $R^c$ of the compound (2), among which trimethylolpropyl group being the most preferred in view of the ease of synthesis.

$R^d$ is preferably the same as those defined for compound (2).

q is preferably 1 in view of the ease of controlling the addition reaction.

X is preferably O in view of economy.

[When p is 4]

When p is 4, the compound (2) is preferably a compound (2-4) represented by the following formula:

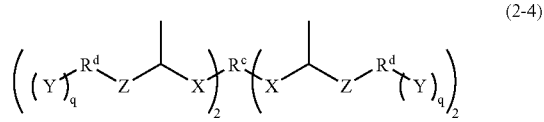

(2-4)

In the formula, symbols are as defined above for the formula (2).

$R^c$ is preferably pentaerythritol.

Such compound (2) is obtained by reacting the vinyl (thio)ether compound (A) having at least one vinyl ether group or vinyl thioether group in the molecule with the compound (B) having at least one thiol group or hydroxyl group and at least one carboxyl group (at least two carboxyl groups in the case of the compound (2-1a)) in the molecule.

The inventors of the present invention found that addition of the carboxyl group to the vinyl group of the vinyl (thio)ether compound (A) takes place in a selective manner when the reaction is allowed to take place at, a low temperature of −10 to 30° C. To be more specific, the inventors found that, in a reaction between, for example, divinyl ether (A) and a thiol (or alcohol) having carboxyl group (namely, a carboxylic acid having thiol group or hydroxyl group)(B), carboxyl group selectively reacts with the vinyl group when the reaction is allowed to take place at such temperature to form hemi(thio)acetal skeleton and a compound having a terminal thiol group (hydroxyl group) is thereby produced.

Compound (2) which has such HS—$R^d$—COO— or HO—$R^d$—COO— in the molecule is a compound wherein intramolecular exchange reaction between the carbonyloxy group (COO) and the terminal thiol group (SH) or the hydroxyl group (OH) takes place by heat.

Among compound (2) wherein p is 2, the compound shown below is particularly preferable since it undergoes the intramolecular exchange reaction as shown below by heating.

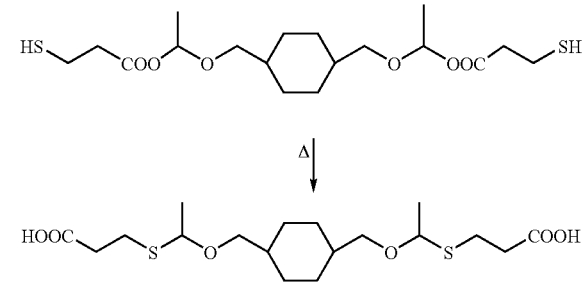

The compound (2-2a) is also a compound wherein intramolecular exchange reaction takes place.

By such intramolecular exchange reaction, compound (2) turns into a compound which has terminal carboxyl group, acetal group, and monothioacetal group or dithioacetal group.

The hemi(thio)acetal ester wherein thioacetal skeleton is produced by the intramolecular exchange reaction between the SH group and the COO group is a precursor for the thioacetal compound of the present invention as described above.

The temperature at which compound (2) undergoes the exchange reaction differs from compound to compound. The temperature, however, is preferably room temperature to 200° C., more preferably room temperature to 150° C., and still more preferably 50 to 100° C. The time required for the exchange reaction is preferably 1 minute to 3 days, more preferably 1 minute to 24 hours, and still more preferably 10 minutes to 5 hours.

Such compound (2) can be favorably used as a latent curing agent for a high molecular weight compound having a group capable of reacting with carboxyl group.

It should also be noted that, in the compound (2), when at least one of Y—$R^d$-Z- is not HS—$R^d$—COO—, X is preferably S.

The compound (2) having such structure has monothioacetal group and/or dithioacetal group in the molecule after the exchange reaction, and further reaction by heating will induce dissociation of the monothioacetal group or the dithioacetal group into vinyl ether group or vinyl thioether group and thiol group. Accordingly, the product produced by curing such compound (2) is a thermally dissociatable cured product which can be disassembled without generating any toxic gas by heating to a temperature lower than the thermal decomposition temperature of the cured product.

As described above, in the case of the compound of the present invention, the exchange reaction takes place within the molecule, and therefore, when the compound of the present invention is used in a one part curing system, the component which is not involved in the reaction will not remain in the system or become discharged from the system, and the problems of tack and toxicity are thereby improved. Accordingly, the compound of the present invention having such properties is adapted for use as a latent curing agent, or a thermally dissociatable material.

This invention also provides third curable composition comprising the compound represented by the formula (2) as described above, and a high molecular weight compound having a group capable of reacting with carboxyl group as a reactive multifunctional compound.

The product produced by curing such curable composition is preferably a thermally dissociatable cured product.

The third curable composition of the present invention is a curable composition comprising the compound (2) and the high molecular weight compound having a group capable of reacting with carboxyl group. The compound (2) is the one as described above, and any adequate compound (2) may be selected depending on the intended use of the composition. The compound (2) may comprise a single compound or a combination of two or more such compound.

The high molecular weight compound used in the composition of the present invention is the one which has a group capable of reacting with carboxyl group. Exemplary preferable such high molecular weight compound include epoxy resins and high molecular weight compounds having carbonate group, oxazolidine group, ester group, maleic group, silanol group, or the like.

Exemplary epoxy resins include bisphenol A epoxy resin, bisphenol F epoxy resin, bisphenol S epoxy resin, biphenyl epoxy resin, naphthalene epoxy resin, novolac epoxy resin, epoxy resin having fluorene skeleton, epoxy resin produced from a copolymer of a phenol compound and dicyclopentadiene, diglycidyl resorcinol, tetrakis(glycidyloxyphenyl)ethane, tris(glycidyloxyphenyl)methane, trisglycidyl aminophenol, triglycidyl aminocrezol, tetraglycidyl xylenediamine and other glycidylamine epoxy resins, vinylciclohexene diepoxide and other alicyclic epoxy resin, and epoxy modified resin, rubber, and other high molecular weight compounds, which may be used alone or in combination of two or more.

In the composition of the present invention, the compound (2) is preferably used at a content (molar ratio) of 0.5 to 1.5 moles, more preferably at 0.7 to 1.3 moles, and still more preferably 0.7 to 1.0 moles per 1.0 mole of the resin. The content of less than 0.5 mole is unfavorable since the composition is less likely to be cured, and the content in excess of 1.5 moles is unfavorable since unreacted curing agent will remain.

The composition of the present invention contains the compound (2), and therefore, the compound (2) has thiol group, hydroxyl group, or carboxyl group bonded on its ends during storing. Under normal storage conditions, these groups are less likely undergo reactions to become cured with resins capable of reacting with carboxyl group, and the composition can be stored in a stable manner. On the other hand, when the composition is heated in the use of the composition, exchange reaction of the compound (2) will take place, and the compound will be converted into a compound having carboxyl group on its ends, and becomes capable of crosslinking with the resin. The composition is thus curable.

As described above, in the case of the composition of the present invention, the crosslinkable compound is produced by the exchange reaction within the molecule in contrast to conventional one part curing system, and therefore, the component which is not involved in the reaction will not remain in the system or become discharged from the system. The problems of tack and toxicity are thereby improved contributing to the maintenance of the global environment.

The temperature to which the composition of the present invention is heated in the use of the composition may vary by the type of the compound (2) used. The temperature of heating, however, is preferably in the range of room temperature to 200° C., more preferably to room temperature to 150° C., and still more preferably to 50 to 100° C. The heating temperature of lower than 50° C. is unfavorable in view of storage stability, and the heating temperature in excess of 100° C. is also unfavorable in view of economy. The heating time is preferably 1 minute to 3 days, preferably 1 minute to 24 hours, and more preferably 10 minutes to 5 hours. In the case of the composition using the compound (2-2), the composition can be cured by heating to about 100° C. for about 30 minutes.

In addition to the compound (2) and the resin having a group which is capable of crosslinking with the carboxyl group, the composition of the present invention may contain a filler, a curing aid, an antiaging agent, a solvent, a plasticizer, or other additives at an amount which does not adversely affect the merit of the present invention.

The composition of the present invention can be produced by ordinary method employed in the art, namely, by mixing the compound (2), the resin having a group which is capable of crosslinking with the carboxyl group, the high molecular weight compound such as rubber, and other additives, and thoroughly kneading the mixture preferably at a reduced pressure for uniform dispersion of the components.

When the composition contains at least one compound which generates monothioacetal group and/or dithioacetal group in the molecule after the exchange reaction as the compound (2), and the product produced by curing the composition of the present invention contains monothioacetal group and/or dithioacetal group, the product produced by curing the composition of the present invention will become softened or liquefied by heating the cured product to a temperature below the thermal decomposition temperature of the cured product, and the cured product can then be readily disassembled. In other words, the composition of the present invention is a composition which is capable of curing into a thermally dissociatable cured product.

The cured product may preferably have a thermal dissociation temperature of 100 to 250° C., preferably 130 to 220° C., and more preferably 150 to 200° C. When the cured product is not dissociated at a temperature in excess of 250° C., working efficiency will be poor and the resin itself will be decomposed with the risk of generating a toxic gas.

The dissociation time is preferably 1 minute to 24 hours, more preferably 1 minute to 5 hours, and still more preferably 1 minute to 2 hours, and dissociation within such period is preferable in view of working efficiency and economy.

When the cured product is thermally dissociatable, and when a member is bonded to another member- or when a member is temporarily bonded to a reinforcement by using the composition of the present invention, the members or the member and the reinforcement can be readily disassembled by heating, and recycling of the member is thereby enabled contributing to the maintenance of the global environment.

EXAMPLES

Next, the present invention is described in further detail by referring to Examples which by no means limit the scope of the invention.

(Model Experiment 1 for Confirming Thermal Dissociation Ability)

In order to confirm the thermal dissociation ability of the addition product of thiol and vinyl ether, a model compound was produced by reacting 1,8-dimercapto-3,6-dioxaoctane and 2 equivalents of isobutyl vinyl ether to thereby synthesize compound e. The resulting compound e was confirmed for its thermal dissociation ability. The reaction scheme is shown below.

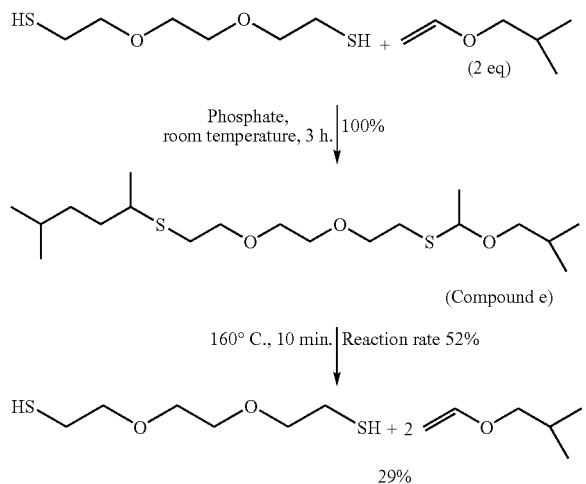

<Synthesis of Compound e>

9.1 g (0.05 mol) of 1,8-dimercapto-3,6-dioxaoctane and 10 g (0.1 mol) of isobutyl vinyl ether were reacted in the presence of a phosphate catalyst at room temperature for 3 hours to obtain 19.1 g (yield, 100%) of the compound e as described above.

δ (H number, assignment) in $^1$HNMR spectrum (chloroform-d) of compound e: 0.9 (12H, $CH_3$), 1.8 (6H, $CH_3$), 1.9 (2H, CH), 2.8 (4H, S—$CH_2$), 3.7 (8H, O—$CH_2$), 4.7 (2H, O—CH).

<Thermal Dissociation Ability>

The resulting compound e was placed in a Kjeldahl flask, and a condenser was mounted on the flask. The compound was heated to 160° C. for 10 minutes while circulating the water. In the measurement of the resulting product by $^1$HNMR, reaction rate of the compound e was found to be 52%, and thiol and vinyl ether which are the thermally dissociated components were found to be 29.5%.

δ (H number, assignment) in $^1$HNMR spectrum (chloroform-d) of the thermally dissociated components
isobutyl vinyl ether: 0.9 (6H, $CH_3$), 2.0 (1H, CH), 3.5(2H, O—$CH_2$), 4.1 (2H, =$CH_2$), 6.5 (1H,=CH).

1,8-dimercapto-3,6-dioxaoctane: 1.7 (2H, SH), 2.8 (4H, S—$CH_2$), 3.7 (8H, O—$CH_2$).

Example 1

<Production of Crosslinked Cured Thioacetal by Self-Crosslinking>

Cyclohexanedimethanol divinyl ether which is a bifunctional vinyl ether compound (A), and a polythiol (product name, Thiokol LP70 (manufactured by Toray Thiokol), SH number5.45, SH equivalent 218) which is a compound (B) having two or more thiol groups in one molecule were mixed such that molar ratio (vinyl ether group/thiol group) of the vinyl ether group in (A) to the thiol group in the component (B) was 1.0. To this mixture was added an acidic phosphate (an acid catalyst (C)) such that weight ratio of the acidic phosphate to the bifunctional vinyl ether was 0.01.

When this composition was heated in an oven to 100° C. for 30 minutes, it lost surface and interior tack, and became cured. When the resulting cured product was heated again in the oven to 160° C., thermal dissociation took place and the cured product could be disassembled after 10 minutes. The results are shown in Table 1.

Example 2

<Production of Crosslinked Cured Thioacetal by Self-Crosslinking>

(A) cyclohexanedimethanol divinyl ether and (B) trimercaptotriazine were mixed such that molar ratio (vinyl ether group/thiol group) of vinyl ether group in (A) to thiol group in (B) was 1.0. To this mixture was added an acidic phosphate such that weight ratio of the acidic phosphate to the bifunctional vinyl ether was 0.01.

When this composition was heated in an oven to 100° C. for 30 minutes, it lost surface and interior tack, and became cured. When the resulting cured product was heated again in the oven to 160° C., thermal dissociation took place and the cured product could be disassembled after 10 minutes. This thermal dissociation temperature was lower than the thermal dissociation temperature which will be described in Example 3. The results are shown in Table 1.

Example 3

<Production of Crosslinked Cured Thioacetal by Self-Crosslinking>

(A) cyclohexanedimethanol divinyl ether and (B) trimercapto-triazine were mixed such that molar ratio (vinyl ether group/thiol group) of vinyl ether group in (A) and thiol group in (B) was 1.0.

When this composition was heated in an oven to 100° C. for 30 minutes, it lost surface and interior tack, and became cured. When the resulting cured product was heated again in the oven to 180° C., thermal dissociation took place and the cured product could be disassembled after 10 minutes. The results are shown in Table 1.

Example 4

<Production of Crosslinked Cured Thioacetal by Self-Crosslinking>

Trifunctional polypropylene glycol (PPG, weight average molecular weight, 3000) and bifunctional vinyl ether (cyclohexanedimethanol divinyl ether) were mixed such that vinyl ether group/hydroxyl group was 2.0 to thereby synthesize a prepolymer having vinyl ether at its end.

The thus synthesized prepolymer having the vinyl ether at its end which is a bifunctional vinyl ether (A) and a polythiol (B) (product name, Thiokol LP70, manufactured by Toray Thiokol); SH number 5.45; SH equivalent 218) were mixed such that molar ratio (vinyl ether group/thiol group) of the vinyl ether group in (A) to the thiol group in the component (B) was 1.0. To this mixture was added an acidic phosphate such that weight ratio of the acidic phosphate to the bifunctional vinyl ether was 0.01.

When this composition was heated in an oven to 100° C. for 30 minutes, it lost surface and interior tack, and became cured. When the resulting cured product was heated again in the oven to 160° C., thermal dissociation took place and the cured product could be disassembled after 20 minutes. The results are shown in Table 1.

Comparative Example 1

Cyclohexanedimethanol divinyl ether and a polyol (product name, PLACCEL 305, manufactured by DAICEL CHEMICAL INDUSTRIES) were mixed such that molar ratio (vinyl ether group/hydroxyl group) of the vinyl ether group to the hydroxyl group in the polyol was 1.0. To this mixture was added an acidic phosphate such that weight ratio of the acidic phosphate to the bifunctional vinyl ether was 0.01. When this composition was heated in an oven to 100° C. for 30 minutes, it lost surface and interior tack, and became cured. When the resulting cured product was heated again in the oven to 160° C., thermal dissociation did not take place. The results are shown in Table 1.

TABLE 1

|  | Example 1 | Example 2 | Example 3 | Example 4 | Comparative Example 1 |
| --- | --- | --- | --- | --- | --- |
| Polythiol (LP70) | 100 |  |  | 100 |  |
| Polyol (PLACCEL 305) |  |  |  |  | 100 |
| Trimercapto-triazine |  | 100 | 100 |  |  |
| Bifunctional vinyl ether | 100 | 100 | 100 |  | 100 |
| Prepolymer having vinyl ether at its end |  |  |  | 100 |  |
| Acidic phosphate | 1 | 1 |  | 1 | 1 |
| Curing temp./time | 100° C./ 30 min. | 100° C./ 30 min. | 100° C./ 30 min. | 100° C./ 30 min. | 100° C./ 30 min. |
| Thermal dissociation temp./time | 160° C./ 10 min. | 160° C./ 10 min. | 180° C./ 10 min. | 160° C./ 20 min. | 160° C., not dissociated |

The numbers in Table 1 represent parts by mass.

Example 5

<Synthesis of Thioacetal Compound>

9.2 g (0.1 mol) of 2-mercaptoethanol and 9.8 g (0.05 mol) of cyclohexanedimethanol divinyl ether were reacted at room temperature for 5 hours in the presence of a phosphate catalyst to produce 19.0 g of the compound a represented by the following formula.

[δ (assignment, H number) in $^1$HNMR (chloroform-d): 1.0–1.8 (cyclohexyl, 10H), 1.5 ($CH_3$, 6H), 2.8 (S—$CH_2$, 4H), 3.2–3.7 (O—$CH_2$, 8H), 4.7 (O—CH, 2H)]

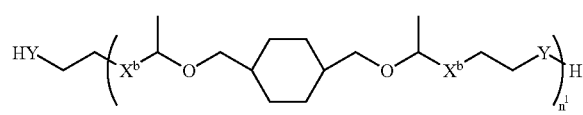

[in the formula, $X^b$ and Y are independently O or S (provided that at least one of $X^b$ is S), and $n^1$ is approximately 1 to 3]

Compound a

<Synthesis of Urethane Polymer>

Trifunctional polypropylene glycol (Mw 3000, manufactured by Asahi Glass Polyurethane K.K., "Excenol 3030") and TDI (manufactured by Mitsui Chemical K.K., "TDI-80/20") were mixed at a NCO/OH ratio of 2.5, and mixture was allowed to react at 90° C. to thereby synthesize urethane polymer.

<Preparation of Curable Composition>

100 parts by mass of the compound a, 100 parts by mass of the urethane polymer, and 0.5 parts by mass of a phosphate (manufactured by Johoku Chemical Industries K.K., "JP502") were mixed to produce the composition.

When this composition was heated to 120° C. for 1 hour, it lost surface tack, and became cured.

The resulting cured product became soft when it was further heated to 170° C. for 20 minutes.

Example 6

<Synthesis of Thioacetal Compound>

18.2 g (0.1 mol) of 1,8-dimercapto-3,6-dioxaoctane and 9.8 g (0.05 mol) of cyclohexanedimethanol divinyl ether were reacted at room temperature for 5 hours in the presence of a phosphate catalyst to produce 28.0 g of compound b represented by the following formula.

[δ (assignment, H number) in $^1$HNMR (chloroform-d): 1.0–1.8 (cyclohexyl, 10H), 1.5 ($CH_3$, 6H), 2.7 (S—$CH_2$, 8H), 3.3–3.8 (O—$CH_2$, 20H), 4.7 (O—CH, 2H)]

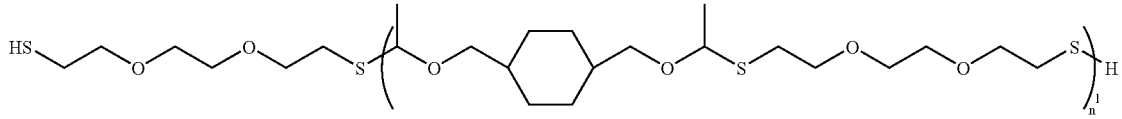

($n^1$ is approximately 1 to 3)

Compound b

<Preparation of Curable Composition>

100 parts by mass of compound b, 100 parts by mass of urethane polymer which was the same as the one used in Example 5, and 0.5 parts by mass of phosphate (manufactured by Johoku Chemical Industries K.K. "JP502") were mixed at room temperature to produce a composition.

When this composition was heated to 120° C. for 1 hour, it lost surface tack, and became cured. The resulting cured product became soft when it was further heated to 170° C. for 20 minutes.

Example 7

<Synthesis of Thiol Having Hemiacetal Ester Skeleton>

53.0 g of 3-mercaptopropionic acid and 49.0 g of cyclohexanedimethanol divinyl ether were reacted at 0° C. to room temperature for 5 hours to produce 102 g of the compound c represented by the following formula.

[δ (assignment, H number) in $^1$HNMR (chloroform-d): 1.0–1.8 (cyclohexyl, 10H), 1.3 (CH$_3$, 6H), 2.6–2.9 (S—CH$_2$, OOC—CH$_2$, 8H), 3.3–3.7 (O—CH$_2$, 4H), 6.0 (CH(q), 2H)].

Compound c

<Preparation of Curable Composition and Cured Product>

28 g (0.01 mol) of the compound c and 14 g (0.01 mol) of epoxy resin (manufactured by ASAHI DENKA, "ED505R") were mixed to produce a composition. When this composition was heated to 100° C. for 30 minutes, it lost surface tack, and became cured. The resulting cured product became soft when it was further heated to 160° C. for 20 minutes.

Example 8

Compound c obtained in Example 7 was heated to 70° C. for 3 hours, and compound d represented by the following formula was produced at an yield of 97%.

[δ (assignment, H number) in $^1$HNMR (chloroform-d): 1.0–1.8 (cyclohexyl, 10H), 1.3 (CH$_3$, 6H), 2.8–3.0 (S—CH$_2$, OOC—CH$_2$, 8H), 3.2–3.7 (O—CH$_2$, 4H), 4.7 (CH(q), 2H)]

Compound d

<Preparation of Curable Composition and Cured Product>

A composition was produced by repeating the procedure of Example 7 except that compound d (28 g, 0.01 mol) was used instead of the compound c.

When this composition was heated to 100° C. for 30 minutes, it lost surface tack, and became cured as in the case of Example 7. The resulting cured product became soft when it was further heated to 160° C. for 20 minutes.

Comparative Example 2

<Preparation of Curable Composition>

4.7 g (0.01 mol) of dithiol (1,8-dimercapto-3,6-dioxaoctane) and 14 g (0.01 mol) of the epoxy resin which was the same as the one used in Example 7 were mixed in a manner similar to Example 7 to produce a composition.

When this composition was heated to 120° C. for 30 minutes, it did not lose surface tack, and did not become cured.

INDUSTRIAL APPLICABILITY OF THE INVENTION

The thermally dissociatable material having thioacetal skeleton which is provided by the present invention is quite useful as a highly disposable plastic material since, when it is used after curing, it can be softened or liquefied at any desired timing by allowing thermal dissociation of the product to take place at a temperature lower than the thermal decomposition temperature of the cured product. In particular, such thermal dissociation enables easy disassembly of the material to which the thermally dissociatable material had been attached, and hence, disassembly of the structure to which the thermally dissociatable material had been attached in a short time.

Such thermally dissociatable material is a curable material which is adapted for use as a sealant, coating composition, or adhesive, and such material may be used, for example, as a curing agent for urethane curable composition or epoxy curable composition, or as a self-curable material. The thermally dissociatable material of the present invention is also expected to be useful as a thermal recording material or a heat storage material which stores heat by heat budget. In the case of uncrosslinked compound, the compound is recyclable into starting materials.

The invention claimed is:

1. A thioacetal compound being thermally dissociatable represented by the following formula (1):

wherein $R^a$ and $R^b$ are independently an aliphatic hydrocarbon group containing 2 to 18 carbon atoms, an alkyl aromatic group containing 7 to 24 carbon atoms, or an aromatic group or a heterocyclic group containing 6 to 18 carbon atoms, said groups optionally containing a substituent or a hetero atom;

n is an integer of 0 to 10;

m in is independently an integer of 1 to 3;

$X^a$ is O; and at least one of $X^b$ is S, and $X^b$ of the remainder are S or O, and YH is SH or OH and at least one of $X^b$ is S and at least one of Y is S.

2. A hemi(thio)acetal ester represented by the following formula (2):

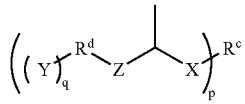
(2)

wherein $R^c$ and $R^d$ are independently an optionally substituted aliphatic hydrocarbon group, aromatic group, alkyl aromatic group, or heterocyclic group containing 2 to 24 carbon atoms, said group optionally containing at least one hetero atom selected from O, S, and N;

p is 1, 2, 3, or 4; and q is 1, 2, or 3;

X is S or O, and each X may be the same or different when p is 2 or more;

Y is SH, OH, or COOH, and each Y may be the same or different when p or q is 2 or more (provided that at least one of Y is SH or OH, and when Y is COOH, only one Y is COOH); and Z is COO, S, or O (provided that at least one of Y is SH or at least one of Z is S), and each Z may be the same or different when p is 2 or more provided that at least one of Y—$R^d$-Z- is HS—$R^d$—COO— or HO—$R^d$—COO—.

3. A hemi(thio)acetal ester according to claim 2 wherein at least one of the Y—$R^d$-Z- is HS—$R^d$—COO—, and thioacetal ester skeleton is generated by intramolecular exchange reaction between said SH group and said COO.

4. A crosslinked cured thioacetal which contains at least one thermally dissociatable monothioacetal and/or dithioacetal skeleton as its site of crosslinking, wherein the monothioacetal and dithioacetal skeleton is derived from the thioacetal compound according to claim 1.

5. A thioacetal compound, a hemi(thio)acetal ester, or a crosslinked cured thioacetal according to any one of claims 1, 2 and 4 which is a derivative of a vinyl (thio)ether compound (A) represented by the following general formula on its terminal,

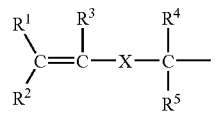

in the formula, $R^1$, $R^2$, $R^3$, $R^4$, and $R^5$ are independently hydrogen atom or an organic group containing 1 to 16 carbon atoms, and $R^1$ or $R^2$ together with $R^4$ or $R^5$ may form a heterocycle, X is oxygen atom or sulfur atom.

6. A composition for producing the thioacetal, the hemi(thio)acetal ester, or the crosslinked cured thioacetal compound of any one of claims 1, 2 and 4 wherein the composition comprises (A) a vinyl (thio)ether compound having at least one vinyl ether and/or vinyl thioether terminal group represented by the following general formula on its terminal,

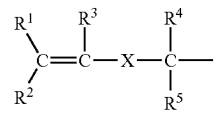

in the formula, $R^1$, $R^2$, $R^3$, $R^4$, and $R^5$ are independently hydrogen atom or an organic group containing 1 to 16 carbon atoms, and $R^1$ or $R^2$ together with $R^4$ or $R^5$ may form a heterocycle, X is oxygen atom or sulfur atom; and (B) a polythiol which contains two or more thiol groups in the molecule.

7. A curable composition comprising
the thioacetal compound of claim 1; and
a multifunctional compound which is capable of reacting with hydroxyl group, thiol group or carboxyl group.

8. A curable composition comprising
the hemi(thio)acetal ester of claim 2 or 3; and
a multifunctional compound which is capable of reacting with carboxyl group.

9. A thermally dissociatable cured product which is produced by crosslinking and curing the curable composition of claim 7.

10. A thioacetal compound, a crosslinked cured thioacetal, or a thermally dissociatable cured product of any one of claims 1, 4 and 9, wherein said thioacetal group thermally dissociates into thiol group and vinyl ether group and/or vinyl thioether group.

11. A composition according to claim 6 wherein said (B) polythiol is an aromatic thiol.

12. A composition according to claim 6 further comprising an acid catalyst (C) selected from the group consisting of a protonic acid, a Lewis acid, an organic tin compound, and a phosphate.

13. A thermally dissociatable cured product which is produced by crosslinking and curing the curable composition of claim 8.

* * * * *